United States Patent [19]

Farooq et al.

[11] 4,443,445
[45] Apr. 17, 1984

[54] IMIDAZO- AND PYRIMIDO-1,3,5-THIADIAZIN-4-ONES

[75] Inventors: Saleem Farooq, Arisdorf; Hans-Peter Streibert, Rheinfelden, both of Switzerland

[73] Assignee: Ciba-Geigy Corporation, Ardsley, N.Y.

[21] Appl. No.: 413,955

[22] Filed: Sep. 1, 1982

[30] Foreign Application Priority Data

Sep. 10, 1981 [CH]  Switzerland ........................ 5859/81
Dec. 10, 1981 [CH]  Switzerland ........................ 7896/81
Aug. 9, 1982 [CH]  Switzerland ........................ 4771/82

[51] Int. Cl.³ .................. C07D 513/04; A01N 43/50; A01N 43/54; A01N 43/88
[52] U.S. Cl. ........................................ 424/246; 544/10
[58] Field of Search ........................... 544/10; 424/246

[56] References Cited

U.S. PATENT DOCUMENTS 4,159,328  6/1979  Ikeda et al. .............................. 544/8

FOREIGN PATENT DOCUMENTS 55-13211  1/1980  Japan ..................................... 544/8
55-53206  4/1980  Japan ..................................... 544/8

Primary Examiner—John M. Ford
Attorney, Agent, or Firm—Frederick H. Rabin

[57] ABSTRACT

The invention relates to novel substituted imidazo- and pyrimido-1,3,5-thiadiazin-4-ones of the formula

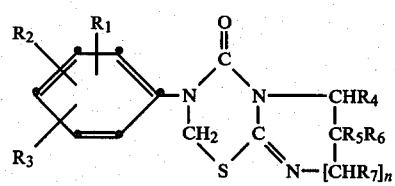

wherein each of $R_1$, $R_2$ and $R_3$ independently of one another is hydrogen, halogen, $C_1$–$C_4$alkyl, trifluoromethyl, $C_1$–$C_4$alkoxy, nitro, benzyl, phenyl, phenoxy, phenylthio, or phenoxy which is substituted by one or two members selected from the group consisting of halogen $C_1$–$C_4$alkyl, trifluoromethyl, nitro, methoxy and ethoxy; each of $R_4$, $R_5$, $R_6$ and $R_7$ independently of one another is hydrogen or $C_1$–$C_4$alkyl; and n is 0 or 1, to the preparation of these novel compounds and to compositions containing them for use in pest control, especially for controlling insects and representatives of the order Acarina which are pests of plants and animals. The novel compounds are particularly effective against larval stages and nymphs of plant-destructive feeding insects, and most particularly against plant destructive cicadas, especially in rice crops.

19 Claims, No Drawings

IMIDAZO- AND PYRIMIDO-1,3,5-THIADIAZIN-4-ONES

The present invention relates to novel unsubstituted or substituted 3-phenyl-2,3,6,7-tetrahydro-4H-imidazo[2,1-b]-1,3,5-thiadiazin-4-ones and 3-phenyl-2,3,7,8-tetrahydro-4,6H-pyrimido[2,1-b]-1,3,5-thiadiazin-4-ones, to the preparation thereof and to the use thereof in pest control.

The novel compounds of this invention have the formula I

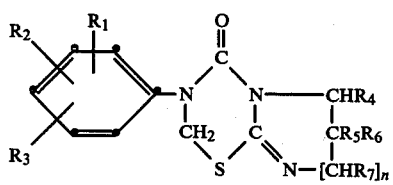

wherein each of $R_1$, $R_2$ and $R_3$ independently of one another is hydrogen, halogen, $C_1$-$C_4$alkyl, trifluoromethyl, $C_1$-$C_4$alkoxy, nitro, benzyl, phenyl, phenoxy, phenylthio, or phenoxy which is substituted by one or two members selected from the group consisting of halogen $C_1$-$C_4$alkyl, trifluoromethyl, nitro, methoxy and ethoxy; each of $R_4$, $R_5$, $R_6$ and $R_7$ independently of one another is hydrogen or $C_1$-$C_4$alkyl; and n is 0 or 1.

Particularly interesting compounds of the present invention are compounds of formula I, wherein each of $R_1$, $R_2$ and $R_3$ independently of one another is hydrogen, fluorine, chlorine or methyl, with hydrogen, fluorine or chlorine being preferred.

Preferred compounds of the formula I are those wherein $R_1$ is in the 2- or 4-position of the phenyl ring, as well as those wherein $R_3$ is hydrogen.

Compounds of the formula I meriting particular interest are also those wherein each of $R_4$, $R_5$, $R_6$ and $R_7$ is hydrogen or methyl, and those wherein n is 0.

On account of their pronounced pesticidal activity, particularly preferred compounds of the formula I are those wherein each of $R_1$, $R_2$ and $R_3$ independently of one another is hydrogen, fluorine, chlorine or methyl, each of $R_4$ and $R_5$ is hydrogen or methyl, $R_6$ is hydrogen, and n is 0.

The present invention also relates to the salts, especially to the salts which are tolerated by plants, of the compounds of formula I. Examples of such suitable salts with organic and inorganic acids are: chlorides, bromides, iodides, sulfates, hydrogensulfates, chlorates, perchloroates, thiocyanates, nitrates, phosphates, hydrogen phosphates, tetrafluoroborates, formates, acetates, trichloroacetates, trifluoroacetates, phenylsulfonates, oxalates, malonates, succinates, malates, tartrates or citrates.

The compounds of formula I, and salts thereof, may be prepared in a manner which is known per se (q.v. German Offenlegungsschrift No. 28 24 126) by reacting a compound of the formula II

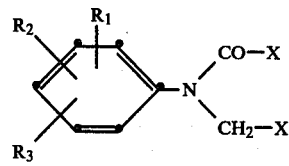

with a compound of the formula III

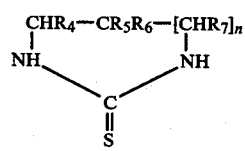

in which formulae $R_1$ to $R_7$ and n are as defined for formula I above and X is halogen, preferably chlorine.

This reaction is normally conducted in the presence of a base to give a free compound of the formula I. If the reaction is carried out without a base, then the corresponding salts, i.e. hydrohalides, are obtained. If required, such hydrohalides may be converted by known methods with other acids into salts of the desired kind. Suitable bases are inorganic bases such as KOH, NaOH, $NH_4OH$ or $NaHCO_3$, as well as organic bases such as trialkylamines, e.g. triethylamine or ethyl diisopropylamine, pyridine, dialkyl anilines etc.

The reaction to give the compounds of the formula I is preferably carried out in a solvent. Examples of suitable solvents are aromatic hydrocarbons such as benzene, toluene and xylene; ketones such as acetone, cyclohexanone and methyl ethyl ketone; ethers such as tetrahydrofuran, dioxan and diethyl ether; halogenated hydrocarbons such as chloroform, carbon tetrachloride and chlorobenzene; alcohols such as ethanol and propanol; esters of aliphatic acids such as ethyl acetate; aliphatic amides such as dimethyl formamide and dimethyl acetamide; dimethyl sulfoxide and other solvents which do not influence the reaction. These solvents may also be employed as mixtures.

The reaction temperature may vary within wide limits from $-10°$ to $+300°$ C. The preferred temperature range is from room temperature to about 200° C.

The starting N-halomethyl-N-phenylcarbamoyl halides of the formula II and thioureas of the formula III are known or may be obtained by methods analogous to known ones (q.v. German Offenlegungsschrift No. 28 24 126; J. Org. Chem. 39, 2897/1974; Chem. Abstr. 59, 9816 ff). For example, a compound of the formula II may be obtained by reacting an aniline of the formula IV with formaldehyde and then reacting the resultant N-methyleneaniline of the formula V with phosgene:

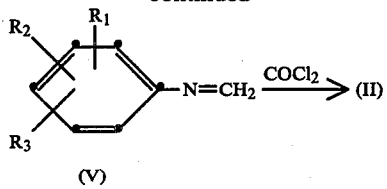

$$\text{(V)}$$

Anilines of the formula IV are known or they may be prepared in a manner similar to that described e.g. in German Offenlegungsschrift 30 34 905.

It is already known from German Offenlegungsschrift No. 28 24 126 that 2-imino-phenyl-tetrahydro-1,3,5-thiadiazin-4-ones which are substituted at the 2-imino group and in the 3-position by alkyl, alkoxy, benzyl or phenyl, are pesticidally active, in particular against insects and mites. Compared with these known compounds, the compounds of the formula I of this invention are novel optionally substituted 3-phenyl-2,3,6,7-tetrahydro-4H-imidazo[2,1-b]-1,3,5-thiadiazin-4-ones and 3-phenyl-2,3,7,8-tetrahydro-4,6H-pyrimido[2,1-b]-1,3,5-thiadiazin-4-ones, both of which have a bicyclic heterocyclic structure. Surprisingly, these compounds have a more potent pesticidal, in particular insecticidal, activity. Surprising too is the very rapid action which the compounds of formula I have in particular against representatives of the order Orthoptera.

In general, the compounds of the formula I are suitable for controlling insects of the orders: Lepidoptera, Coleoptera, Homoptera, Heteroptera, Diptera, Thysanoptera, Orthoptera, Blattaria, Anoplura, Siphonaptera, Mallophaga, Thysanura, Isoptera, Psocoptera and Hymenoptera.

The compounds of formula I are furthermore suitable for controlling representatives of the order Acarina of the families: Ioxididae, Argisidae, Tetranychidae and Dermanyssidae. The compounds of formula I may be employed with success in particular for controlling phytopathogenic mites, e.g. of the families Tetranychidae and Phytoptipalpidae (spider mites), Tarsonemidae (soft-bodied mites) and Eriophydiae (gall mites).

In addition to their action against mites and flies, e.g. Aedes aegypti and Musca domestica, the compounds of formula I are also suitable for controlling plant-destructive feeding insects in ornamentals and crops of useful plants, especially in cotton (e.g. against Spodoptera littoralis and Heliothis virescens) and in cereals, fruit and vegetables (e.g. against Laspeyresia pomonella, Leptinotarsa decemlineata and Epilachna varivestis). The compounds of formula I are also very effective against larval insect stages and nymphs, especially of harmful feeding insects. In particular, the compounds of formula I may be very successfully employed against plant-destructive cicadas, especially in rice crops.

Furthermore, the compounds of formula I may be used for controlling ectoparasitic insects and acarids in domestic animals and productive livestock, e.g. by treating animals, cowsheds, barns, stables etc., and pastures.

The activity of the compounds of formula I and of the compositions containing them may be substantially broadened and adapted to prevailing circumstances by addition of other insecticides and/or acaricides. Examples of suitable additives are representatives of the following classes of compounds: organophosphorus compounds, nitrophenols and derivatives thereof, formamides, ureas, pyrethroids, carbamates, chlorinated hydrocarbons, and Bacillus thuringiensis preparations. Compounds of formula I may be combined with particular advantage with diazinon, dioxacarb, heptenophos and isoprocarb to obtain effective insecticidal compositions which are suitable in particular for controlling destructive insects in rice crops.

The compounds of the formula I, and accordingly also the salts thereof, are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. Like the nature of the compositions, the methods of application, such as spraying, atomising, dusting, scattering or pouring, are chosen in accordance with the intended objectives and the prevailing circumstances.

The formulations, i.e. the compositions containing the compound of the formula I or a combination thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil: or water.

The solid carriers used e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, or combination thereof with other insecticides or acaricides, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyl taurin salts.

More frequently, however, so-called synthetic surfactants are used, especially fatty sulfonates, fatty sulfates, sulfonated benzimidazole derivatives of alkylarylsulfonates.

The fatty sulfonates or sulfates are usually in the form of alkyli metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylene-diaminepropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenol polyethoxyethanols, castor oil polyglycol ethers, polypropylene/polyoxyethylene adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methyl sulfates or ethyl sulfates, e.g. stearyl trimethylammonium chloride or benzyl di-(2-chloroethyl)ethylammonium bromide.

The surfactants customarily employed in the art of formulation are described e.g. in "McCutcheon's Detergents and Emulsifiers Annual", MC Publishing Corp., Ringwood, N.J., 1979, and Sisely and Wood, "Encyclopedia of Surface Active Agents", Chemical Publishing Co., Inc. New York (1979).

The pesticidal formulations usually contain 0.1 to 99%, preferably 0.1 to 95%, of a compound of the formula I or combination thereof with other insecticides or acaricides, 1 to 99,9% of a solid or liquid adjuvant, and 0 to 25%, preferably 0.1 to 20%, of a surfactant.

Whereas commercial products are preferably formulated as concentrates, the end user will normally employ dilute formulations containing a lower concentration of active ingredient.

The formulations may also contain further additives such as stabilisers, antifoams, viscosity regulators, binders, tackifiers and fertilisers or other active ingredients in order to obtain special effects.

Formulation Examples for liquid active ingredients of the formula I or combinations thereof with other insecticides or acaricides (throughout, percentages are by weight)

| 1. Emulsifiable concentrates | (a) | (b) | (c) |
|---|---|---|---|
| active ingredient or active ingredient combination | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexane | — | 15% | 20% |
| xylene mixture | 65% | 25% | 20% |

Emulsion of any required concentration can be produced from such concentrates by dilution with water.

| 2. Solutions | (a) | (b) | (c) | (d) |
|---|---|---|---|---|
| active ingredient or active ingredient combination | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| ligroin (boiling range 160–190°) | — | — | 94% | — |

These solutions are suitable for application in the form of microdrops.

| 3. Granulates | (a) | (b) |
|---|---|---|
| active ingredient or active ingredient combination | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | (a) | (b) |
|---|---|---|
| active ingredient or active ingredient combination | 2% | 5% |
| highly dispersed silicic acid | 1% | 5% |
| talcum | 97% | — |
| kaolin | — | 90% |

Ready for use dusts are obtained by intimately mixing the carriers with the active ingredient.

Formulation examples for solid active ingredients of the formula I or combinations thereof with other insecticides or acaricides (throughout, percentages are by weight)

| 5. Wettable powders | (a) | (b) | (c) |
|---|---|---|---|
| active ingredient or active | 25% | 50% | 75% |

| 5. Wettable powders | (a) | (b) | (c) |
|---|---|---|---|
| ingredient combination | | | |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 6. Emulsifiable concentrate | |
|---|---|
| active ingredient or active ingredient combination | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentration by dilution with water.

| 7. Dusts | (a) | (b) |
|---|---|---|
| active ingredient or active ingredient combination | 5% | 8% |
| talcum | 95% | — |
| kaolin | — | 92% |

Ready for use dusts are obtained by mixing the active ingredient with the carriers, and grinding the mixture in a suitable mill.

| 8. Extruder granulate | |
|---|---|
| active ingredient or active ingredient combination | 10% |
| sodium lignosulfonate | 2% |
| carboxymethylcellulose | 1% |
| kaolin | 87% |

The active ingredient is mixed and ground with the adjuvants, and the mixtures is subsequently moistened with water. The mixture is extruded and then dried in a stream of air.

| 9. Coated granulate | |
|---|---|
| active ingredient or active ingredient combination | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 10. Suspension concentrate | |
|---|---|
| active ingredient or active ingredient combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 1

A reaction vessel is charged at room temperature with 6.1 g (0.06 mole) of N,N'-ethylene thiourea, 50 ml of dimethyl formamide and 15.5 g (0.12 mole) of diisopropylamine. A solution of 12.2 g (0.06 mole) of N-chloromethyl-N-phenylcarbamoyl chloride in 60 ml of methylene chloride is then added dropwise to the above mixture. The reaction mixture is stirred for about 16 hours at room temperature. For working up, the reaction mixture is poured into water and extracted twice with ethyl acetate. The combined ethyl acetate phases are washed 4 times with water and twice with saturated sodium chloride solution, dried over sodium sulfate and concentrated. The crude product is then recrystallised from methylene chloride/hexane to give the desired compound of the formula

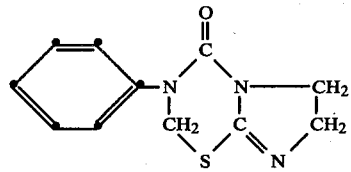

with a melting point of 130°–132° C. (compound 1).

The following compounds of formula I are prepared in corresponding manner:

| Compound | $R_1$ | $R_2$ | $R_3$ | $R_4$ | $R_5$ | $R_6$ | $R_7$ | n | Physical data |
|---|---|---|---|---|---|---|---|---|---|
| 2 | 2-Cl | H | H | H | H | H | — | 0 | m.p. 132–133° C. |
| 3 | 3-Cl | H | H | H | H | H | — | 0 | m.p. 108–109° C. |
| 4 | 4-Cl | H | H | H | H | H | — | 0 | m.p. 175–177° C. |
| 5 | 2-Cl | 4-Cl | H | H | H | H | — | 0 | m.p. 82–85° C. |
| 6 | H | H | H | H | H | H | H | 1 | m.p. 104–105° C. |
| 7 | 4-F | H | H | H | H | H | — | 0 | viscous mass |
| 8 | H | H | H | H | —$CH_3$ | H | — | 0 | m.p. 108–109° C. |
| 9 | H | H | H | —$CH_3$ | H | H | — | 0 | m.p. 101–102° C. |
| 10 | H | H | H | H | —$CH_3$ | —$CH_3$ | — | 0 | m.p. 117–118° C. |

-continued

| Compound | R₁ | R₂ | R₃ | R₄ | R₅ | R₆ | R₇ | n | Physical data |
|---|---|---|---|---|---|---|---|---|---|
| 11 | 2-Cl | H | H | H | H | H | H | 1 | viscous mass |
| 12 | 2-Cl | H | H | H | —CH₃ | —CH₃ | — | 0 | m.p. 115–120° C. |
| 13 | 3-Cl | H | H | H | H | H | H | 1 | m.p. 137–140° C. |
| 14 | 3-Cl | H | H | H | —CH₃ | —CH₃ | — | 0 | m.p. 132–133° C. |
| 15 | 4-Cl | H | H | H | H | H | H | 1 | m.p. 145–148° C. |
| 16 | 4-Cl | H | H | H | —CH₃ | —CH₃ | — | 0 | m.p. 141–143° C. |
| 17 | 2-Cl | 4-Cl | H | H | H | H | H | 1 | m.p. 125–127° C. |
| 18 | 2-Cl | 4-Cl | H | H | —CH₃ | —CH₃ | — | 0 | viscous mass |
| 19 | 2-Cl | H | H | H | —CH₃ | —CH₃ | H | 1 | m.p. 118–120° C. |
| 20 | 4-F | H | H | H | H | H | H | 1 | m.p. 143–145° C. |
| 21 | 4-F | H | H | H | —CH₃ | H | — | 0 | mixture of isomers |
| 22 | 4-F | H | H | —CH₃ | H | H | — | 0 | viscous mass |
| 23 | 2-F | H | H | H | H | H | — | 0 | m.p. 148–150° C. |
| 24 | 2-F | H | H | H | —CH₃ | H | — | 0 | mixture of isomers |
| 25 | 2-F | H | H | —CH₃ | H | H | — | 0 | viscous mass |
| 26 | 2-F | H | H | H | —CH₃ | —CH₃ | — | 0 | m.p. 143–145° C. |
| 27 | 2-F | H | H | H | H | H | H | 1 | viscous mass |
| 28 | 2-F | H | H | H | —CH₃ | —CH₃ | H | 1 | viscous mass |
| 29 | 2-CH₃ | 3-CH₃ | 6-CH₃ | H | H | H | — | 0 | m.p. 58–63° C. |
| 30 | 2-CH₃ | 3-CH₃ | 6-CH₃ | H | —CH₃ | —CH₃ | — | 0 | viscous mass |
| 31 | 2-CH₃ | 3-CH₃ | 6-CH₃ | H | H | H | H | 1 | viscous mass |
| 32 | 2-CH₃ | 3-CH₃ | 6-CH₃ | H | —CH₃ | —CH₃ | H | 1 | m.p. 108–112° C. |
| 33 | 4-CF₃ | H | H | H | H | H | — | 0 | |
| 34 | 4-CH₃ | H | H | H | H | H | — | 0 | |
| 35 | —OCH₃ | H | H | H | H | H | — | 0 | |
| 36 | 2-CH₃ | 6-CH₃ | H | H | H | H | — | 0 | |
| 37 | 4-Br | H | H | H | H | H | — | 0 | |
| 38 | 2-C₂H₅ | 6-CH₃ | H | H | H | H | — | 0 | |
| 39 | 2-CH(C₂H₅)(CH₃) | 6-CH₃ | H | H | H | H | — | 0 | |
| 40 | 4-CH₂-C₆H₅ | 2-CH₃ | 6-CH₃ | H | H | H | — | 0 | |
| 41 | 4-O-C₆H₅ | 2-CH₃ | 6-CH₃ | H | H | H | — | 0 | |
| 42 | 4-O-CH(CH₃)₂ | H | H | H | H | H | — | 0 | |
| 43 | 4-Cl | H | H | H | —CH₃ | H | H | 1 | |
| 44 | 4-Cl | H | H | —CH₃ | H | H | —CH₃ | 1 | |
| 45 | H | H | H | —CH₃ | —CH₃ | H | — | 0 | |
| 46 | H | H | H | —CH₃ | —CH₃ | —CH₃ | — | 0 | |
| 47 | 4-Cl | H | H | —CH₃ | —CH₃ | —CH₃ | — | 0 | |

EXAMPLE 2

Action against *Laodelphax striatellus* and *Nilaparvata lugens* (nymphs)

The test is carried out with growing plants. The procedure is that 4 rice plants (thickness of stem 8 mm) about 20 cm in height are planted into each of a number of pots (diameter 8 cm). The plants in each pot are sprayed on a rotary table with 100 ml of a solution of the test compound in acetone at a concentration of 400 and 800 ppm respectively. After the spray coating has dried, each plant is populated with 20 nymphs of the test organisms in the third stage. To prevent the cicadas from escaping, a glass cylinder is slipped over each of the plants and sealed with a gauze top. The nymphs are kept for 10 days on the treated plant until the next development stage has been reached. Evaluation of percentage mortality is made 1, 4 and 8 days respectively after treatment by means of a comparison with untreated controls.

The following results are obtained with nymphs of *Nilaparvata lugens* after 8 days using compounds of the formula I at a concentration of 400 ppm:

| Compound | Mortality |
|---|---|
| 1 | 85% |
| 2 | 100% |
| 4 | 60% |
| 21 and 22 (mixture of isomers) | 65% |
| 29 | 80% |

Very good results are also obtained with compounds of the formula I using nymphs of *Laodelphax striatellus*.

EXAMPLE 3

Ovicidal action against *Laodelphax striatellus* and *Nilapavarta lugens*

The test is carried out with growing plants. The procedure is that 4 rice plants (thickness of stem 8 mm) about 20 cm in height are planted into each of a number of pots (diameter 8 cm). The plants in each pot are sprayed on a rotary table with 100 ml of a solution of the test compound in acetone at a concentration of 400 ppm. After the spray coating has dried, each plant is populated with 3 adult females. To prevent the cicades from escaping, a glass cylinder is slipped over each of the plants and sealed with a gauze top. The females are kept on the treated plants for 4 days for oviposition and then removed. The young cicadas hatch about 8 days after population of the plants and a count is then made. The percentage mortality is assessed by comparing the number of hatched larvae on the treated plants with the number of those on the untreated controls. In this test, the compounds of formula I have a good ovicidal action.

What is claimed is:

1. A compound of the formula I

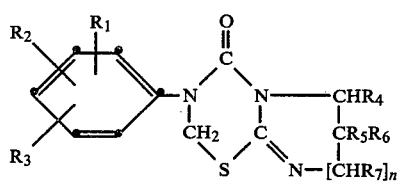

wherein each of $R_1$, $R_2$ and $R_3$ independently of one another is hydrogen, halogen, $C_1$-$C_4$alkyl, trifluoromethyl, $C_1$-$C_4$-alkoxy, nitro, benzyl, phenyl, phenoxy, phenylthio, or phenoxy which is substituted by one or two members selected from the group consisting of halogen $C_1$-$C_4$alkyl, trifluoromethyl, nitro, methoxy and ethoxy; each of $R_4$, $R_5$, $R_6$ and $R_7$ independently of one another is hydrogen or $C_1$-$C_4$alkyl; and n is 0 or 1, or a salt thereof.

2. A compound of the formula I according to claim 1, wherein each of $R_1$, $R_2$ and $R_3$ independently of one another is hydrogen, fluorine, chlorine or methyl.

3. A compound of the formula I according to claim 2, wherein each of $R_1$, $R_2$ and $R_3$ independently of one another is hydrogen, fluorine or chlorine.

4. A compound of the formula I according to claim 3, wherein each of $R_2$ and $R_3$ is hydrogen.

5. A compound of the formula I according to claim 1, wherein $R_1$ is in the 2- or 4-position of the phenyl ring.

6. A compound of the formula I according to claim 1, wherein each of $R_4$, $R_5$, $R_6$ and $R_7$ independently of one another is hydrogen or methyl.

7. A compound of the formula I according to claim 6, wherein each of $R_4$, $R_5$, $R_6$ and $R_7$ is hydrogen.

8. A compound of the formula I according to claim 1, wherein n is O.

9. A compound of the formula I according to claim 5, wherein each of $R_1$, $R_2$ and $R_3$ is hydrogen, fluorine, chlorine or methyl, each of $R_4$ and $R_5$ is hydrogen or methyl, $R_6$ is hydrogen and n is O.

10. The compound according to claim 9 of the formula

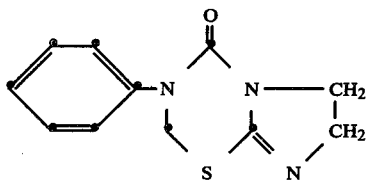

11. The compound according to claim 9 of the formula

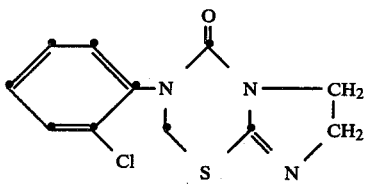

12. The compound according to claim 9 of the formula

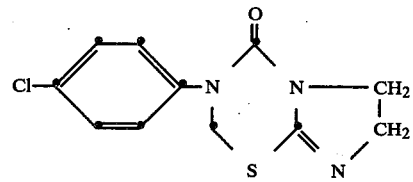

13. The compound according to claim 9 of the formula

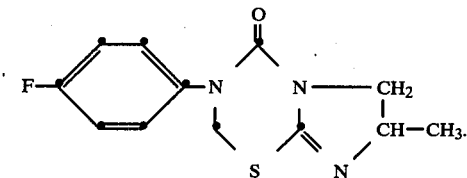

14. The compound according to claim 9 of the formula

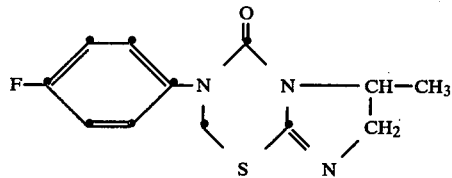

15. The compound according to claim 9 of the formula

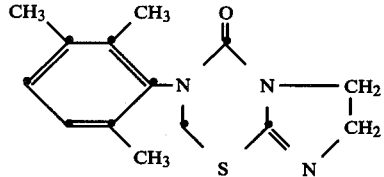

16. A composition for controlling plant destructive insects and representatives of the order Acarina, which contains as active component a pesticidally effective amount of a compound as claimed in claim 1, together with suitable carriers and/or other adjuvants.

17. A method of controlling plant destructive insects and representatives of the order Acarina, which comprises applying to said insects or to the locus thereof a pesticidally effective amount of a compound as claimed in claim 1.

18. A method according to claim 17, wherein the pests to be controlled are plant-destructive cicadas.

19. A method according to claim 18, wherein the pests to be controlled are cicadas in rice crops.

* * * * *